United States Patent
Lederman et al.

(10) Patent No.: US 6,224,540 B1
(45) Date of Patent: May 1, 2001

(54) PASSIVE GIRDLE FOR HEART VENTRICLE FOR THERAPEUTIC AID TO PATIENTS HAVING VENTRICULAR DILATATION

(75) Inventors: David M. Lederman, Marblehead; Robert T. V. Kung, Auburn, both of MA (US)

(73) Assignee: Abiomed, Inc., Danvers, MA (US)

( * ) Notice: Subject to any disclaimer, the term of this patent is extended or adjusted under 35 U.S.C. 154(b) by 0 days.

(21) Appl. No.: 09/023,592

(22) Filed: Feb. 13, 1998

Related U.S. Application Data

(60) Division of application No. 08/581,051, filed on Dec. 29, 1995, now Pat. No. 5,800,528, which is a continuation-in-part of application No. 08/490,080, filed on Jun. 13, 1995, now Pat. No. 5,713,954.

(51) Int. Cl.$^7$ ...................................................... A61F 2/04

(52) U.S. Cl. ............................................................ 600/37

(58) Field of Search .................................. 623/3; 600/16, 600/17, 37; 601/153; 607/123, 129

(56) References Cited

U.S. PATENT DOCUMENTS

| | | | |
|---|---|---|---|
| 2,826,193 | * 3/1958 | Vineberg | 601/153 |
| 3,464,322 | 9/1969 | Pequignot . | |
| 3,587,567 | 6/1971 | Schiff | 128/24.5 |

(List continued on next page.)

FOREIGN PATENT DOCUMENTS

| | | | |
|---|---|---|---|
| 0370931 | 5/1990 | (EP) | 601/151 |
| 2645739 | 10/1990 | (FR) . | |
| 2115287 | 9/1983 | (GB) . | |
| 2271829 | 4/1989 | (JP) . | |
| 1009457 | * 4/1983 | (SU) | 623/3 |
| 1734767 | 5/1992 | (SU) | 600/16 |

OTHER PUBLICATIONS

Anstadt, G.L. et al. "A New Instrument for Prolonged Mechanical Cardiac Massage" *Circulation 31 and 32 suppl II:* II–43–II–44 (1965).

Anstadt, M.P. et al "Pulsatile Reperfusion After Cardiac Arrest Improves Neurologic Outcome" *Annals of Surg 214(4)*:478–490 (1991);.

Bencini, A. et al. "The 'Pneumomassage' of the Heart" *Surgery 39*:375–384 (1956).

Capouya E.R. et al. "Girdling Effect Of Nonstimulated Cardiomyoplasty On Left Ventricular Function" *Ann. Thorac Surg. 56*:867–871 (1993).

Carpentier, A. et al "Dynamic Cardiomyoplasty At Seven Years" *J. Thorac and Cardiovasc Surg 106(1)*:42–54 (1993).

Carpentier, A. et al. "Mycardial Substitution with a Stimulated Skeletal Muscle: First Successful Clinical Case" *Lancet 1*:1267 (1985).

Chekanov, V. "Nonstimulated Cardiomyoplasty Wrap Attenuated The Degree of Left Ventricular Enlargement" *Ann. Thorac. Surg. 57*:1684 91984).

Kass D.A. et al. "Reverse Remodeling from Cardiomyoplasty in Human Heart Failure" *Circulation 91*:2314–2318 (1995).

Vaynblat et al., *Cardiac Binding in Experimental Heart Failure*, The Society of Thoracic Surgeons: 1997 Annual Meeting, pp. 81–85, 1997.

Vaynblat, et al., *Cardiac Binding in Experimental Heart Failure*, Abstract 1810, Supplement 1, Circulation, vol. 92, No. 8, p. I–380, Oct. 15, 1995.

Primary Examiner—David H. Willse
(74) Attorney, Agent, or Firm—Thomas J. Engelenner; Nutter, McClennen & Fish, LLP

(57) ABSTRACT

A passive girdle is wrapped around a heart muscle which has dilatation of a ventricle to conform to the size and shape of the heart and to constrain the dilatation during diastole. The girdle is formed of a material and structure that does not expand away from the heart but may, over an extended period of time be decreased in size as dilatation decreases.

20 Claims, 4 Drawing Sheets

U.S. PATENT DOCUMENTS

| | | | |
|---|---|---|---|
| 3,613,672 | 10/1971 | Schiff | 601/153 X |
| 4,536,893 | 8/1985 | Parravicini | 623/3 |
| 4,628,937 | 12/1986 | Hess et al. . | |
| 4,690,134 | 9/1987 | Snyders | 128/64 |
| 4,827,932 | 5/1989 | Ideker et al. . | |
| 4,936,857 | 6/1990 | Kulik . | |
| 4,957,477 | 9/1990 | Lundbäck | 600/16 |
| 5,098,369 | 3/1992 | Heilman et al. | 600/16 |
| 5,119,804 | 6/1992 | Anstadt | 601/153 |
| 5,131,905 | 7/1992 | Grooters | 600/16 |
| 5,336,254 | 8/1994 | Brennen . | |
| 5,383,840 | 1/1995 | Heilman . | |
| 5,534,024 | 7/1996 | Rogers et al. . | |
| 5,713,954 | 2/1998 | Rosenberg et al. . | |
| 5,800,528 | 9/1998 | Lederman et al. . | |

* cited by examiner

PASSIVE GIRDLE FOR HEART VENTRICLE FOR THERAPEUTIC AID TO PATIENTS HAVING VENTRICULAR DILATATION

This invention is a divisional application of U.S. patent application Ser. No. 08/581,051 filed Dec. 29, 1995, now U.S. Pat. No. 5,800,528, which is a continuation-in-part of U.S. patent application Ser. No. 08/490,080 filed Jun. 13, 1995, now U.S. Pat. No. 5,713,954. The contents of patent application Ser. No. 08/490,080 are specifically incorporated herein by reference.

BACKGROUND OF THE INVENTION

Patients having a heart condition known as ventricular dilatation are in a clinically dangerous condition when the patients are in an end stage cardiac failure pattern. The ventricular dilatation increases the load on the heart (that is, it increases the oxygen consumption by the heart), while at the same time decreasing cardiac efficiency. A significant fraction of patients in congestive heart failure, including those who are not in immediate danger of death, lead very limited lives. This dilatation condition does not respond to current pharmacological treatment. A small amount, typically less than 10%, of the energy and oxygen consumed by the heart, is used to do mechanical work. Thus the balance, which is the major part of the energy consumed by the heart is used in maintaining the elastic tension of the heart muscles for a period of time. With a given pressure, the elastic tension is directly proportional to the radius of curvature of the heart ventricle. During ventricular dilatation the ventricular radius increases and the energy dissipated by the heart muscle just to maintain this elastic tension during diastole is abnormally increased, thereby increasing oxygen consumption. A number of methods and devices have been employed to aid the pumping action of failing hearts. Many of these include sacs or wraps placed around the failing heart, or, in some instances only around the ventricle of the failing heart, with these wraps constructed to provide for active pumping usually, but not always, in synchronism with the ventricular pumping of the natural heart. Table 1 lists a number of developed devices with pertinent operating characteristics.

TABLE 1

| Device | Level of Support | Pulsatility | Duration | Blood Contacting | Comments |
|---|---|---|---|---|---|
| IABP | Partial <20% | Y | Days to Months | Y | Counterpulsation provides LV unloading |
| Biopump | Full | N | Days | Y | Limited to short duration due to thrombotic potential |
| Thoractec | Full | Y | Months | Y | Sac-type actuation |
| Novacor | Full | Y | Months | Y | Sac-type pump with electric actuation |
| Hemopump | Partial 50–75% | N | Days | Y | Axial flow pump |
| Heart Mate | Full | Y | Months | Y | Pusher-Plate pneumatic and electric |
| Aortic Patch | Partial | Y | Months | Y | Counterpulsation |
| BVS 5000 | Full | Y | Weeks | Y | Designed for temporary support |
| Anstadt | Full | Y | Days | N | Cardiac resuscitation |
| Cardiomyoplasty | Partial <20% | Y | Years | N | Requires muscle training |

One, more recent development involves the wrapping and pacing of a skeletal muscle around the heart to aid in the pumping. In that configuration, a pacemaker is implanted to control the timing of the activation of the wrapped around skeletal muscle.

It is an object of this invention to provide a completely passive girdle to be wrapped around a heart suffering from ventricular dilatation to limit this dilatation and thus improve the performance characteristics of the heart.

It is another object of this invention to provide a passive girdle or vest which can, over a period of time, have its diameter decreased to effect some decrease in dilatation of the ventricle.

Other objects will become apparent in accordance with the description of the preferred embodiments below.

SUMMARY OF THE INVENTION

Ventricular dilatation is a clinically dangerous condition for end stage cardiac failure patients. The output of the heart is effected by: (a) end-diastolic volume (ventricular volume at the end of the filling phase), (b) end-systolic volume (ventricular volume at the end of the ejection phase), and (c) heart rate. When (a) is very large, (b) also tends to be larger and (c) tends to be larger than normal. All three of these factors contribute to large increases in the tension-time integral and therefore to increased oxygen consumption.

Only a small amount of the energy consumed by the heart is used to do mechanical work. For example, with a cardiac output of 5 liters/minute, and $\Delta p$ of 100 mm(Hg), the mechanical work done by the left ventricle is about 1.1 watts, and that of the right ventricle is about 0.2 watts. This compares with the typical total energy consumed by the heart (mechanical work during systole plus the energy cost in maintaining elastic tension during diastole) of about 13.2 to 15 watts.

Thus, since cardiac efficiency (typically between 3% and 15%) is defined as the ratio of the mechanical work done by the heart to the total energy (or load of the heart muscle): then, Cardiac Efficiency, $$\eta = \frac{\int P_v dV}{\int P dV + k \int T dt} \quad (1)$$

$P_V$: Ventricle Pressure
P: Pressure
V: Volume
T: Tension
t: Time
The constant K accounts for conversion of units.

An increase in mechanical work by a large factor results in a small increase in oxygen consumption but an increase in tension time causes a large increase in oxygen consumption. Patients with dilated ventricles who have undergone active cardiomyoplasty have not been reported to show any objectively measurable hemodynamic improvement.

Broadly speaking in the present invention a completely passive girdle is wrapped around the ventricle or the entire heart muscle, and sized so that it constrains the dilatation during diastole and does not effect the action of the ventricle during systole. With the present surgical techniques, it is expected initial access to the heart to place the girdle in position, will require opening the chest. However, it may be possible to locate a girdle in position without thoracotomy. In one embodiment, a synthetic girdle made from material that can limit tension, but is otherwise deformable to conform to the anatomical geometry of the recipient heart is used. This girdle may be adjustable in size and shape over an extended period of time in order to gradually decrease the ventricular dilatation. A second embodiment employs a fluid filled passive wrap constructed of a series of horizontal sections. This provides for a variable volume to be enclosed by the wrap with volume control being obtained by controlling the volume of fluid from an implantable reservoir within the body. In its most preferable form, this passive wrap can be formed of a series of horizontal tubular segments each individually sealed and attached to one another along the long axis of the cylinder. If the cylinders are made of indistensible material, then changing the volume of fluid from the cylinders being in a substantially deflated condition to one where they are partially or fully inflated, decreases the internal perimeter of the wrap or girdle, thereby decreasing the effective radius of the girdle around the heart. Another feature of the invention is a feedback system, wherein sensors, for example, strain gauges, can be built into an indistensible lining to measure its tension and thereby provide automatic feedback to a hydraulic circuit controlling the wrap volume.

To avoid the problem of potential irritability and damage to the external myocardium cells by virtue of the artificial wrap and its long term constraining contact with the myocardium, one embodiment of the invention employs a tissue engineered lining to protect the myocardium. This tissue engineered lining consists of a polymer scaffold seeded with myocardial cells harvested from the patient's own myocardium using tissue engineering technology. That lining then generates a biological myocardio-interfacing surface and remains firmly attached to the polymer interfacing with the surface from which the wrap is made. Such a lining would integrate biologically to the heart's myocardial cells in a manner analogous to other devices currently being investigated which use cell scaffolds for in vitro and in vitro tissue engineering.

DESCRIPTION OF PREFERRED EMBODIMENTS

Figure 1A:
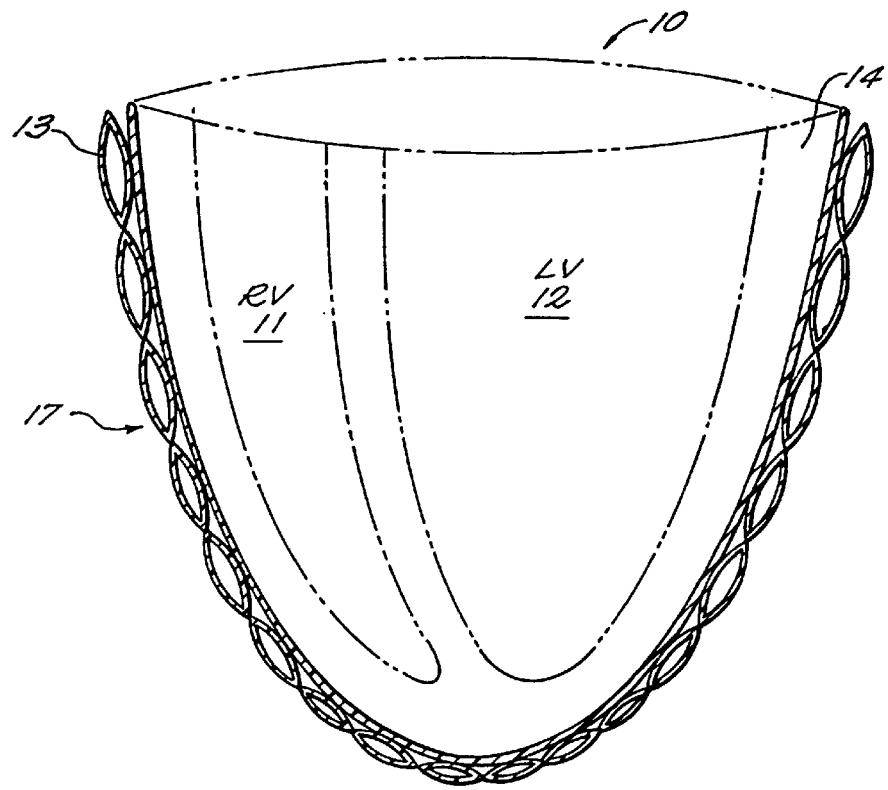
FIG. 1A is an illustration generally in cross sectional form of a heart girdle constructed in accordance with the principles of this invention.
Figure 1B:
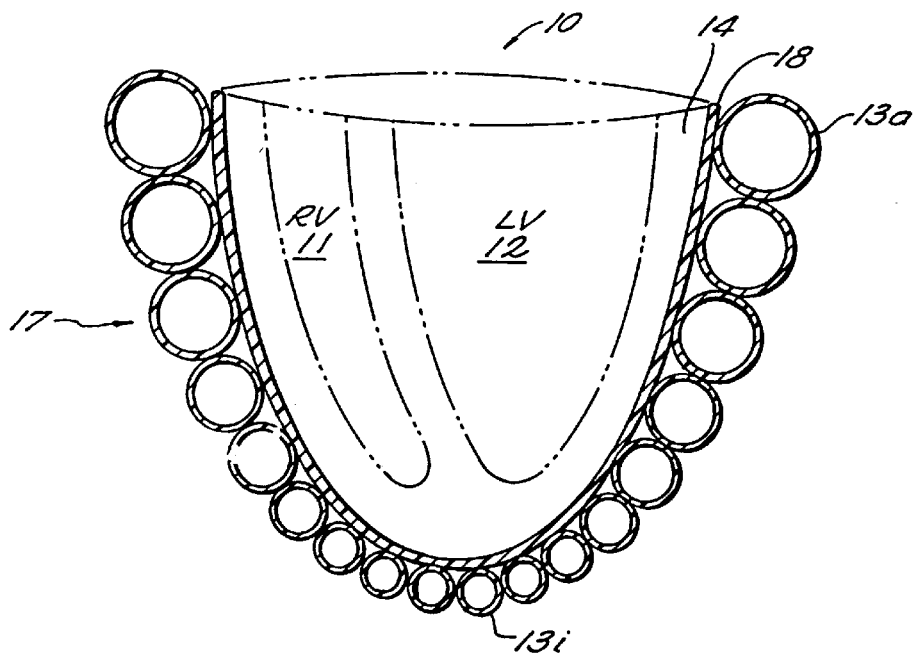
FIG. 1B is an illustration in cross-sectional form of the heart girdle of FIG. 1A with the girdle in a pneumatically filled condition.

In FIGS. 1A and 1B there is illustrated one embodiment of a girdle for wrapping around a heart to constrain dilatation of the ventricle and limit the amount of energy and oxygen required to maintain the heart muscle in tension.

Figure 2:
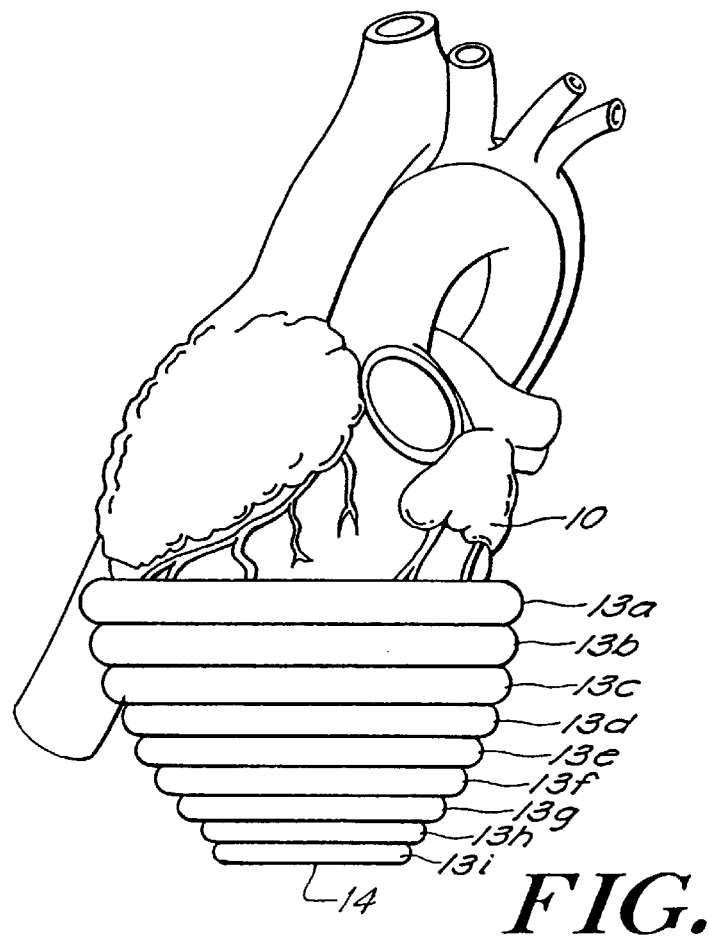
FIG. 2 is a perspective view of a variation of the heart girdle of FIGS. 1A and 1B showing the horizontal segments.
Figure 3:
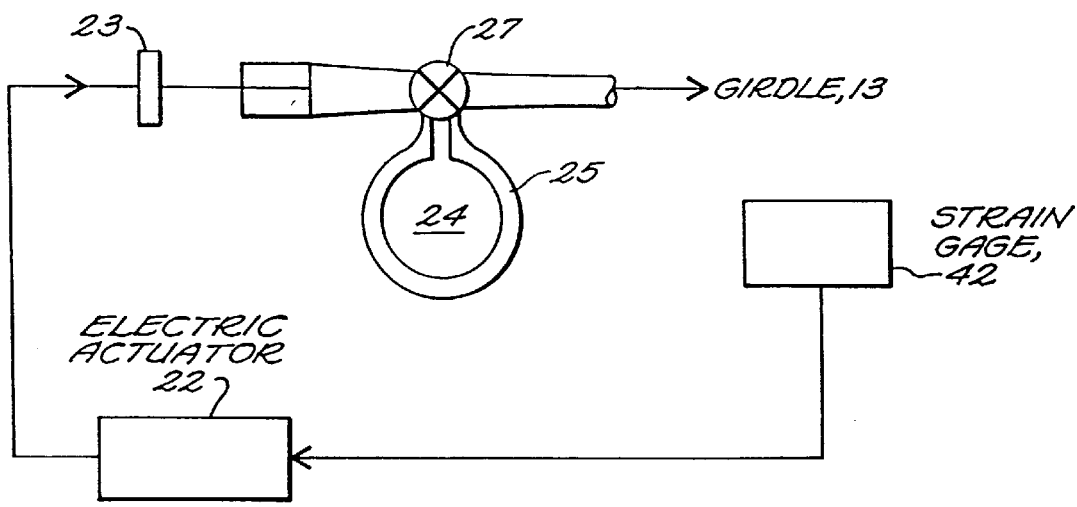
FIG. 3 is an illustration generally in block diagram form of a control system for the heart girdle of FIG. 1 including a strain gauge and electronic actuator to maintain constant tension at the interface between the girdle and the heart muscle.

In FIG. 1A the natural heart 10 is shown with the left ventricle 12 somewhat dilated and with a girdle 17 surrounding both the left ventricle 12 and the right ventricle 11. The girdle 17 is formed as illustrated in FIG. 2, with a series of horizontal segments 13a–13i encircling the heart 10, the segments toward the apex of the heart being smaller in cross section and in length. The girdle segments 13 are filled with hydraulic fluid which is maintained at a constant volume during the beating of the heart. The girdle may additionally be formed with an open apical end 14. In this arrangement the girdle is entirely passive and a distensible girdle lining 18 conforms to the shape of the heart at the myocardium-girdle lining interface by virtue of the pressure of the fluid filled segments 13 against the distensible inner lining 18. As shown in FIG. 3, when this girdle is implanted around a natural heart the volume is controlled through a three-way valve 27 which controls the amount of fluid supplied to the girdle segments 13 from reservoir 25, which is formed of a rigid casing 24.

According to equation (1), it can be seen that an increase in mechanical work by a large factor results in a small increase in oxygen consumption, but an increase in tension time causes a large increase in oxygen consumption. Passive girdling of the heart, as illustrated in FIGS. 1–3, acts to limit or reduce the ventricular size of the diseased ventricle. Over an extended period of time, which may be days or weeks, the fluid 14 volume may be increased, thereby decreasing the periphery of the interface lining 18 of the girdle, which may over a period of time actually decrease the dilatation of the ventricle 12.

In FIG. 3 a control system for controlling the fluid pressure in the segments 13 according to the tension in liner 18 is shown. The fluid pressure in girdle 17 is controlled by a feedback loop including a strain gauge 42 placed at the interface between the inner lining 18 and the myocardium providing a sensed value for the tension of the myocardium, to hydraulic actuating electronics 22 which may be a conventional hydraulic control circuit. The electronic actuator 22 controls a conventional mechanical fluid actuator 23 which provides for increase or decrease of fluid within the girdle 17. This actuator operates in conjunction with a three-way valve 27 and fluid reservoir 25. The change in volume effected by this feedback, is not intended to, nor does it operate in the time frame of the beating of the natural heart. It is meant to adjust the volume over a much longer time period, typically days, weeks or months.

In this configuration, the series of generally cylindrical segments 13 are typically formed of non-distensible material. They are attached to one another along the long axis of the cylinder and may be filled with fluid either individually or in parallel. When the fluid volume within the compartments 13 is very low, then the girdle 13 assumes the shape shown in FIG. 1A providing for a large inner diameter. On the other hand, when the fluid volume is increased the segments assume, at full inflation, a circular cross section thereby decreasing the inner perimeter very substantially, as illustrated in FIG. 1B. Thus, by controlling the volume of the fluids supplied to the individual segments 13, the inner diameter of the girdle 17 can be adjusted to be a close fit to the natural heart. This configuration has the advantage that, since there is no single vertical compartment, there is no gravity pooling of fluid in one portion of the girdle 17.

Figure 4:
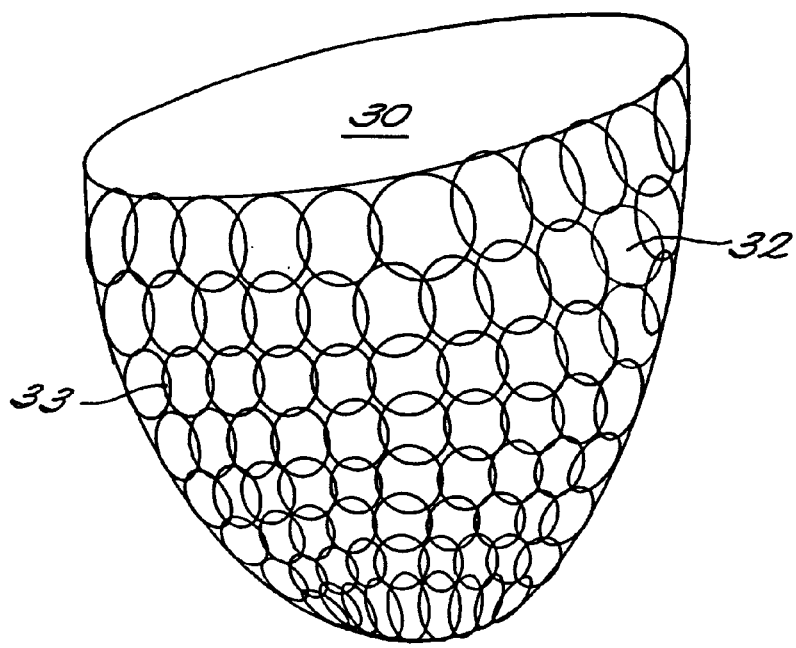
FIG. 4 is an illustration in perspective view of a heart girdle employing a flexible mesh of interlocked circular plastic loops.

FIG. 4 illustrates a second embodiment of this invention. The girdle 30 of FIG. 4 is an adjustable girdle made from a synthetic material that can limit tension, but is otherwise deformable to conform to the anatomical geometry of the heart. In this case, the girdle 30 is formed of a confining net 32 which is wrapped around the heart from the apex to the atrioventricular (A-V) groove. The purpose of this net is to limit the maximum diastolic dimension of the heart, while offering no resistance to systolic ejection. In the design illustrated in FIG. 4 a number of interlinked two-dimensional loops such as lightweight plastic rings 33 are interconnected to form the girdle or wrap 30. The loops 33 are free to move in all directions without restraint, since none are physically connected to each other. Rather, they are interlocked by having the loops or rings 33 pass through one another. The design of FIG. 4 presents no systolic load to the contracting heart. The loop-mesh 32 can readily conform to the shape of the heart with the change in surface area accompanying the heart contraction readily accommodated by the free loops.

Figure 5:
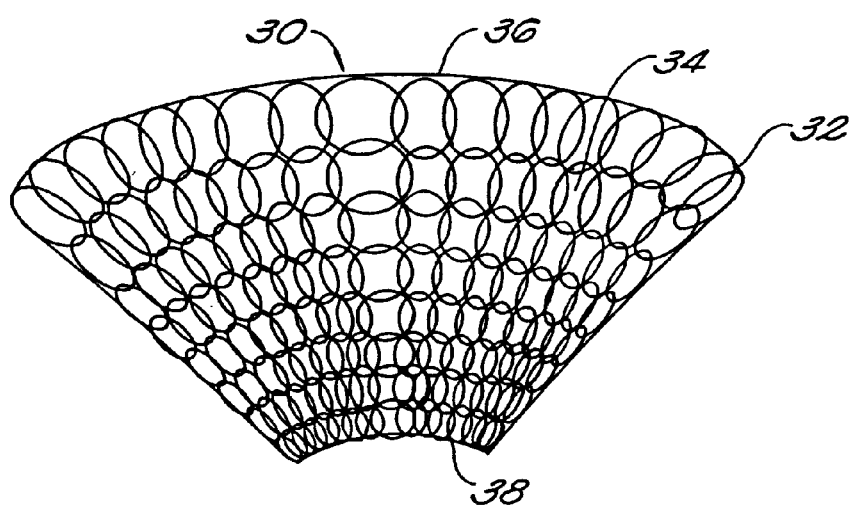
FIG. 5 is an illustration of a portion of a girdle constructed generally in accordance with the girdle construction of FIG. 4, but further including strings adapted to draw the girdle into decreasing diameter shape.
Figure 6:
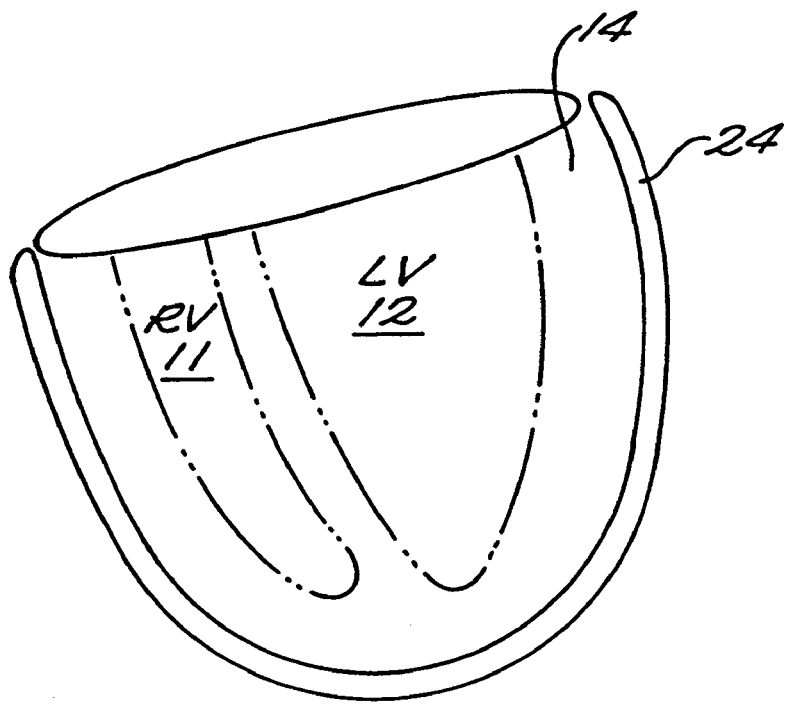
FIG. 6 is another embodiment of a portion of a passive girdle formed of a material characterized by a specific internal structure.

An alternative form of this loop-mesh girdle is shown in FIG. 5. In FIG. 5 a string system 34 is included with the string attached to the loops 32 to effect change in the size of the mesh by virtue of pulling the strings. This arrangement is able to accommodate a treatment modality for scheduled size reduction to the heart over a suitable period of time. In FIG. 5, a segment of the girdle or wrap 30 is shown. The original size of the wrap can be seen at the wide edge 36, while the narrowed down section is seen at the ridge 38 of the wrap. Pulling on the two ends of two sets of strings reduces the size of the mesh in two directions. This can be done during a thoracoscopy or through a cutaneous access port. In the construction illustrated in FIGS. 4 and 5 the net 30 will be attached at several attachment points, typically 4 to 6 in number, at the A-V groove and also perhaps near the apex of the natural heart. At the original implant the surgeon will optimize the fit to the heart as it is existing and will adjust the size through the mechanism described above. This design will accommodate spontaneous heart size reduction even though some parts of the mesh may adhere to the epicardium. However, due to relative motion between the loops, it is unlikely that the mesh will become fully encapsulated. In FIG. 6 there is shown a girdle in accordance with this invention which is formed of a sheet of an expanded polytetrafluroethylene material 24, prestressed such that it remains below its elastic limit and its tension in the plane of the sheet is sufficient to create radially inward forces, thus resisting expansion while permitting inward compression. In other words the girdle will resist further expansion while fittingly accommodating shrinkage. Other materials may be employed, provided that they exhibit the above elasticity characteristics.

Figure 7:
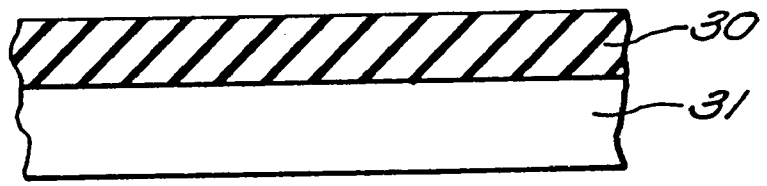
FIG. 7 is a cross sectional drawing of a girdle-myocardium interface constructed of biologically engineered myocardial tissue.

In FIG. 7 there is illustrated a cross sectional view of a tissue engineered girdle lining having a polymer scaffold 31 which has been seeded with myocardial cells harvested from the recipient mounted on a polymer substrate 31, the substrate either facing a girdle structure or forming the inner surface of that girdle. The tissue engineered lining faces the patient's myocardium. Such a lining reduces the irritation which may occur between the epicardium and artificial materials employed to form the girdle itself. The lining 30 would, over time, integrate biologically to the patient's myocardium.

Techniques for cell scaffold engineering are described in the literature. Two examples being, Biodegradable Polymer Scaffolds for Tissue Engineering by Lisa E. Freed, Gordana Vunjak-Novakovic, Robert J. Biron, Dana B. Eagles, Daniel C. Lesnoy, Sandra K. Barlow and Robert Langer and Tissue by Robert Langer and Joseph P. Vacanti, Biotechnology, Vol. 12, July 1994 and Tissue Engineering, Robert Langer and Joseph P. Vacanti, Science, Vol. 260 May 14, 1993.

This tissue engineering techniques may also be employed with respect to other artificial materials which come in contact with the heart in various surgical situations including the active devices described in U.S. patent application Ser. No. 08/490,080, filed Jun. 13, 1995.

Having described the above specific embodiments of this invention, other embodiments implementing the concepts of this invention will doubtless occur.

What is claimed is:

1. An apparatus configured to provide passive radial resistance to a hypertrophic heart having a circumference and a major axis running from the apex to the top of the heart, said apparatus comprising:

a wrap member configured to conformingly surround at least a portion of the circumference of the heart when in operable configuration, said wrap member having a constraining material wherein, when said wrap member is in said operable configuration, said wrap member provides a passive sustained dimensional constraint on a heart muscle and wherein said constraining material is adjustable such that it can be configured to resist expansion of the heart beyond one of a plurality of predetermined inner perimeters of said wrap member without resistance to systolic ejection.

2. The apparatus of claim 1, wherein said constraining material comprises a net structure that, upon fitting around at least a portion of a heart, limits diastolic expansion of the heart.

3. The apparatus of claim 2, wherein said net structure is further interconnected by strings extending in at least a first dimension such that pulling on said strings to decreases the dimension of said wrap member in position around the patient's heart.

4. The apparatus of claim 1, wherein the apparatus further comprises:

at least one strain gauge adapted to measure girdle tension.

5. The apparatus of claim 1, wherein the apparatus further comprises:

adjustment means for adjusting said constraining material to set a desired inner perimeter;

at least one strain gauge adapted to measure girdle tension; and means for providing a feedback control signal to said adjustment means.

6. The apparatus of claim 1, wherein said wrap member further comprises:

at least one fluidically sealed segment.

7. The apparatus of claim 6, wherein said at least one fluidically sealed segment has a plurality of inflation states between a substantially fully inflated state and a substantially fully uninflated state.

8. The apparatus of claim 7, wherein the sustained dimensional constraint of said wrap member is determined by said inflation state of said at least one fluidically sealed segment.

9. The apparatus of claim 6, wherein said wrap member comprises:

a plurality of fluidically sealed segments.

10. The apparatus of claim 9, wherein said fluidically sealed segments are adapted to be oriented substantially perpendicularly to the major axis of the heart.

11. The apparatus of claim 10, wherein said wrap member, when in said operative configuration, is adapted to define open ends adjacent the top and the bottom of the heart.

12. The apparatus of claim 1, further comprising:

means for adjusting said constraining material to set a desired inner perimeter.

13. The apparatus of claim 12, wherein said constraining material comprises a mesh net material and the adjustment means further comprises means for tightening the mesh net material to limit diastolic expansion of the heart.

14. The apparatus of claim 12, wherein said wrap member further comprises at least one fluidically sealed segment, and wherein said adjusting means changes a volume of fluid provided to said at least one fluidically sealed segment.

15. The apparatus of claim 1, wherein the apparatus further comprises:

a distensible lining adapted to lie between the wrap member and the natural heart.

16. The apparatus of claim 15, wherein said lining comprises a tissue engineered lining having a polymer scaffold seeded with cells.

17. The apparatus of claim 16, wherein the cells comprise myocardial cells.

18. The apparatus of claim 16, wherein the cells comprise a cellular wall.

19. An apparatus configured to provide passive radial resistance to a hypertrophic heart, said apparatus comprising:

a wrap member configured to conformingly surround at least a portion of the circumference of the heart when in operable configuration, the wrap member having a plurality of segments of constraining material that provide, when the wrap member is in said operable configuration, a passive, sustained dimensional constraint on a heart muscle.

20. An apparatus configured to provide passive radial resistance to a hypertrophic heart, said apparatus comprising:

a wrap member configured to conformingly surround at least a portion of the circumference of the heart when in operable configuration, the wrap member having a constraining material that provides, when the wrap member is in said operable configuration, a passive, sustained dimensional constraint on a heart muscle; and a sensor for sensing tension in the wrap member.

* * * * *

UNITED STATES PATENT AND TRADEMARK OFFICE
CERTIFICATE OF CORRECTION

PATENT NO. : 6,224,540 B1
DATED : May 1, 2001
INVENTOR(S) : Lederman et al.

It is certified that error appears in the above-identified patent and that said Letters Patent is hereby corrected as shown below:

Column 5,
Line 64, reads "polytetrafluroethylene material" should read -- polytetrafluoroethylene material --

Column 6,
Line 55, reads "strings to decreases" should read -- strings decreases --

Signed and Sealed this

Twenty-ninth Day of January, 2002

Attest:

JAMES E. ROGAN
Attesting Officer
Director of the United States Patent and Trademark Office